United States Patent [19]

Niimura et al.

[11] Patent Number: 5,411,964
[45] Date of Patent: May 2, 1995

[54] PHENYLALANINE-GLYCINE COMPOUNDS HAVING ANTI-TUMOR ACTIVITY, PROCESS FOR PREPARATION THEREOF, AND PHARMACEUTICAL COMPOSITION CONTAINING SAID COMPOUNDS

[75] Inventors: Koichi Niimura; Takako Kawabe, both of Saitama; Takao Ando; Kenichi Saito, both of Tokyo, all of Japan

[73] Assignee: Kureha Chemical Industry Co., Ltd., Tokyo, Japan

[21] Appl. No.: 31,478

[22] Filed: Mar. 15, 1993

[30] Foreign Application Priority Data

Mar. 14, 1992 [JP] Japan .................. 4-089564

[51] Int. Cl.$^6$ .............. A61K 31/505; A61K 31/215; C07D 239/12; C07C 229/28
[52] U.S. Cl. .................. 514/269; 514/274; 514/533; 514/534; 514/538; 514/539; 514/542; 514/563; 544/311; 544/312; 544/313; 560/21; 560/22; 560/29; 560/32; 562/445; 562/448
[58] Field of Search ............ 544/312, 311, 313; 514/269, 563, 274, 533, 534, 638, 539, 542; 560/632, 29, 21, 22; 562/445, 448

[56] References Cited

U.S. PATENT DOCUMENTS

| | | | |
|---|---|---|---|
| 2,713,045 | 7/1955 | Wieland et al. | 560/32 X |
| 2,927,107 | 3/1960 | Vellur et al. | 562/448 X |
| 3,062,804 | 11/1962 | Albertson | 560/32 X |
| 4,025,644 | 5/1977 | Miki et al. | 424/300 |
| 4,029,547 | 6/1977 | Umezawa et al. | 562/448 X |
| 4,216,208 | 8/1980 | DeBarbieri | 536/53 X |
| 4,250,183 | 2/1981 | Krastinat | 562/448 X |
| 4,315,851 | 2/1982 | Yoshikumi et al. | 424/85 |
| 4,401,592 | 8/1983 | Yoshikumi et al. | 424/85 |
| 4,737,518 | 4/1988 | Nomura et al. | 544/312 X |
| 4,871,870 | 10/1989 | Kim | 560/39 |
| 4,925,662 | 5/1990 | Ogachi et al. | 424/85.91 |
| 5,081,284 | 1/1992 | Higuchi et al. | 560/159 |
| 5,130,474 | 7/1992 | Makovec et al. | 562/448 |
| 5,142,048 | 8/1992 | Hemmi et al. | 544/172 |

FOREIGN PATENT DOCUMENTS 0013891 8/1908 European Pat. Off. ......... 536/53

OTHER PUBLICATIONS

Tetrahedron Letters, vol. 32, No. 27, 1991, pp. 3163-3166, "Conversion of Serine and Threonine Residues Into α-Acyloxy-, α-Alkylthio-, and α-Halogenoglyucine Moieties: . . . Modification of Peptides" Apitz et al.

J. Biochem. (Tokyo), vol. 77, No. 1, 1975, pp. 69–79, Hayashi et al. "Kinetic Studies of Carboxypeptidase Y" Hayashi et al.

Journal of Controlled Release, vol. 18, No. 2, 1992, pp. 123–132, Subr et al, "Polymers containing enzymatically degradable bonds, XII. Effect of spacer structure . . . activity measured in vivo" Subr et al.

*Primary Examiner*—Floyd D. Higel
*Attorney, Agent, or Firm*—Sughrue, Mion, Zinn, Macpeak & Seas

[57] ABSTRACT

A phenylalanine-glycine compound of formula (I):

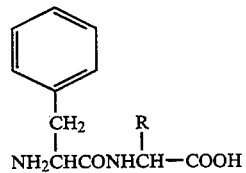

(I)

wherein R represents a residue of an antitumor substance, or a salt or ester thereof, a process for preparation thereof, and a pharmaceutical composition containing the same are described. The novel conjugate of the phenylalanine-glycine compound and the antitumor substance exhibits superior antitumor activity in comparison with the case wherein an antitumor substance is administered alone or as a mixture with phenylalanine.

14 Claims, No Drawings

PHENYLALANINE-GLYCINE COMPOUNDS HAVING ANTI-TUMOR ACTIVITY, PROCESS FOR PREPARATION THEREOF, AND PHARMACEUTICAL COMPOSITION CONTAINING SAID COMPOUNDS

BACKGROUND OF THE INVENTION

1. Field of the Invention

The present invention relates to a novel conjugate of a phenylalanine derivative with an antitumor substance, a process for preparation thereof, and a pharmaceutical composition, in particular, an antitumor agent, containing it. More particularly, the present invention relates to a conjugate of L-phenylalanine-glycine with an antitumor substance, a process for preparation thereof, and a pharmaceutical composition containing it.

2. Description of the Related Art

Hitherto, chemotherapeutic agents have proved efficacious in treating tumors, but many problems still remain. For example, chemotherapeutic agents not only have effects on tumor cells, but also affect the host cells and exhibit cell toxicity. Therefore, the agents cannot be administered for a long time to physically weakened patients and thus it was difficult to secure a sufficient therapeutic effect. The mechanism of action of chemotherapeutic agents is based on the inhibition of biosynthesis (in particular, that of nucleic acids) in the cells and inhibition of the metabolism necessary to maintain cell life. That is, the chemotherapeutic agents were not specific to the tumor. Namely, these agents were toxic to the general cells of the host suffering from the tumor as well as toxic to the tumor cells. It was desired to develop antitumor agents with an improved selectivity to the tumor cells and an improved method for concentrating conventional antitumor agents into the tumor cells.

While 5-fluorouracil (5-FU) alone does not exhibit antitumor activity, 5-FU exhibits antitumor activity when bonded with penrose phosphate in the cells to form fluorodeoxyuridine-5'-monophosphate (FdUMP), fluorouridine-5'-triphosphate (FUTP) or the like. Namely, FdUMP inhibits the thymidylate synthetase activity to inhibit the synthesis of DNA. FUTP is taken up in an RNA and causes critical damage to the RNA, thereby inhibiting the production of cell proteins. Therefore, if the pentose phosphate in the tumor cells could be increased selectively, selective chemotherapy to tumor cells would become possible by using 5-FU.

Further, pyruvate kinase is the rate-determining enzyme in the anaerobic glycolysis which relates to the production of pentose phosphate in the cells, and includes L-type, $M_1$-type, and $M_2$-type isoenzymes. Tumors contain almost only $M_2$-type isoenzyme. It was known that the $M_2$-type isoenzyme is selectively inhibited by a low concentration of L-phenylalanine. Therefore, it was expected that L-phenylalanine could cause inhibition specific to the pyruvate kinase activity in the tumor cells and enhance the production of penrose phosphate only in the tumor cells. Thus, Lee disclosed and ascertained a method of enhancing the activity of 5-FU to inhibit the tumor in combination with L-phenylalanine [Med. J. Kagoshima Univ., Vol. 37, No. 3-4, 285-308, 1985].

In the method of Lee, however, L-phenylalanine was mixed in a laboratory chew and ingested. 5-FU was separately administered. Therefore, L-phenylalanine and 5-FU were conveyed separately to the lesion. The present inventors engaged in various studies with the object of conveying L-phenylalanine and 5-FU to the target lesion in a bonded form and separating them quickly at the target site. As a result, the inventors found that the above object can be achieved by bonding 5-FU with L-phenylalanine-1-acetoxyglycine, and that there is a similar effect in antitumor substances other than 5-FU. The present invention is based on these findings.

SUMMARY OF THE INVENTION

Accordingly, the present invention relates to a phenylalanine-glycine compound of the formula (I)

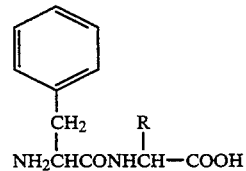

(I)

wherein R represents a residue of an antitumor substance, a salt thereof or an ester thereof (hereinafter sometimes referred to as the "the present conjugate"), a process for preparation of the present conjugate, and a pharmaceutical composition containing the present conjugate.

DETAILED DESCRIPTION OF THE PREFERRED EMBODIMENTS

The glycine moiety contained in the present conjugate may be any residue of L- or D-glycine, or a mixture of LD-glycine. Further, the phenylalanine moiety is preferably a residue of L-phenylalanine, but may also be residue of D-phenylalanine or a mixture of LD-phenylalanine. The present conjugate may be a nontoxic salts or esters which the amino acids in the glycine and/or phenylalanine residues can form.

The nontoxic salts may be acid-addition salts or metal complexes. The metal complexes are complexes with, for example, zinc, iron, calcium, magnesium, or aluminum. As the acid-addition salts, there may be mentioned hydrochloride, hydrobromide, sulfate, phosphate, tannate, oxalate, fumarate, gluconate, alginate, maleate, acetate, trifluoroacetate, citrate, benzoate, succinate, malate, ascotbate, tartrate, or the like. Further, the salts may be carbonates, for example, salts with alkali metals (sodium, potassium salts, etc.), salts with alkaline earth metals (calcium, magnesium salts, etc.), or ammonium salts.

The esters may be any esters conventionally used for amino acids, such as aryl or alkyl esters. In particular, there may be mentioned straight-chain or branched alkyl esters having 1 to 4 carbon atoms, such as methyl, ethyl, n-propyl, isopropyl, n-butyl, or isobutyl ester.

The antitumor substance residue R in the present conjugate may be a residual group of an alkylating antitumor substance, an antimetabolic antitumor substance, an antibiotic antitumor substance, or the like. As the antitumor substances, there may be mentioned, for example, 5-fluorouracil, 5-amino-7-hydroxy-1H-v-triazolo(4,5-d)pyrimidine, 4-amino-$N^{10}$-methylpteroyl-glutamic acid, 4-aminopteroyl-glutamic acid, 6-mercaptopurine, 5-[bis(2-chloroethyl)amino]-uracil, mitomycin C, bleomycin, daunorubicin, doxorubicin, p-[bis(2-chloroethyl)amino]-L-phenylalanine or ester thereof, N,N-bis(2-chloroethyl)-N¹, O-propylene-phosphate ester diamine, 4-[p-(bis(2-chloroethyl)amino)phenyl]-butylic acid or ester thereof.

The present conjugate may be prepared by the steps (a) and (b) as follows:

(a) The step comprising introducing an antitumor substance residue R into a compound of the formula (IIIb):

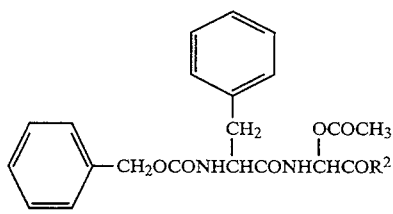

(IIIb)

wherein R² represents a benzyloxy group or an alkoxy group with 1 to 4 carbon atoms, to obtain a compound of the formula (II):

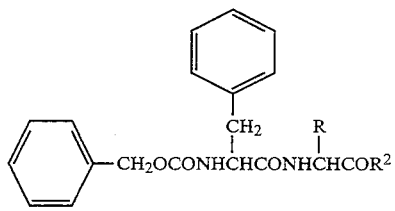

(II)

wherein R and R² have the same meanings as above.

(b) The step comprising removing group(s) for protecting amino group(s) from the compound of the formula (II) to obtain the compound of the formula (I) or ester thereof.

In the step (a), the compound of the formula (IIIb) and the antitumor substance are reacted in the presence of an organic solvent (for example, dimethylformamide) and preferably a base at −10° to 50° C., preferably at 10° to 30° C., for 10 to 120 minutes, preferably for 15 to 60 minutes, to thereby obtain the compound of the formula (II). As the base, triethylamine, pyridine or the like may be used. After the reaction is completed, the reaction product is used in the next step without or with purification by recrystallization, distillation, extraction, precipitation, washing, column separation, concentration, lyophilization, or the like. In the step (b), a solution of the compound of the formula (II) in an organic solvent is added to an alcohol solution of palladium carbon and treated at −10° to 120° C., preferably at −5° to 100° C., for 10 to 300 minutes, preferably for 15 to 240 minutes. After cooling, the filtrate is concentrated to obtain the crystal. Further, the crystal was recrystallized or washed with a solvent to obtain a compound of the formula (I) with a high purity. If necessary, the D-form and L-form of the compound of the formula (I) or ester thereof are resolved from each other by, for example, chromatography. The compound of the formula (I) may be converted to the corresponding salt or ester before being used as an antitumor agent.

Examples of the present conjugate include:
(1) L-phenylalanyl-2-(5-fluorouracil-1-yl)-D,L-glycine
(2) L-phenylalanyl-2-(5-fluorouracil-1-yl)-D,L-glycineamide
(3) L-phenylalanyl-2-(5-fluorouracil-1-yl)-D,L-glycinemethylester
(4) L-phenylalanyl-2-(5-fluorouracil-1-yl)-D,L-glycineethylester
(5) L-phenylalanyl-2-(5-fluorouracil-1-yl)-D,L-glycinepropylester
(6) L-phenylalanyl-2-[5-(bis(2-chloroethyl)-amino)-uracil-1-yl]-D,L-glycine
(7) L-phenylalanyl-2-[5-(bis(2-chloroethyl)amino)-uracil-1-yl]-D,L-glycinemethylester
(8) L-phenylalanyl-2-[5-(bis(2-chloroethyl)amino)-uracil-1-yl]-D,L-glycineethylester
(9) L-phenylalanyl-2-[p-(bis(2-chloroethyl)amino)-L-phenylalaninemethylester-2-yl]-D,L-glycineethylester
(10) L-phenylalanyl-2-(5-fluorouracil-1-yl)-L-glycine
(11) L-phenylalanyl-2-(5-fluorouracil-1-yl)-D-glycine The compound of the formula (IIIb) may be prepared, for example, by the following steps (c) to (e):

(c) The step comprising reacting a salt of a compound of the formula (V):

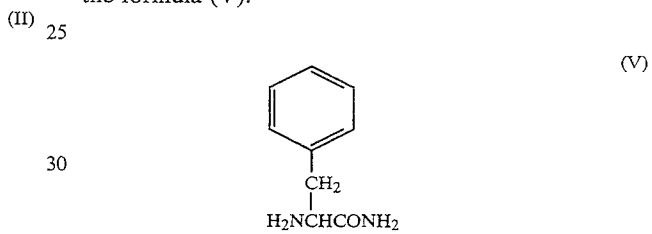

(V)

with carbobenzoxychloride to obtain a compound of the formula (IV):

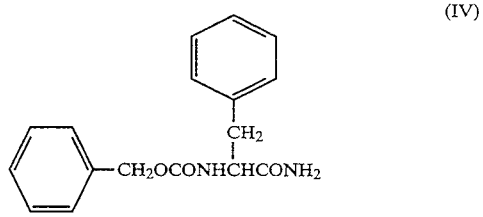

(IV)

More particularly, L-phenylalanineamide hydrochloride and sodium hydrogencarbonate are dissolved in water and then carbobenzoxychloride and an organic solvent are added at 0° to 30° C. The mixture is agitated and reacted, for 1 to 24 hours, preferably for 2 to 8 hours. Further carbobenzoxychloride and sodium hydrogencarbonate may be added thereto. After the reaction is completed, a white crystal is taken out and recrystallized from ethyl acetate to obtain the compound of the formula (IV).

(d) The step comprising reacting the compound of formula (IV) with a glyoxylic acid compound of the formula (VI):

(VI)

wherein R² has the same meaning as above, to obtain a compound of the formula (IIIa):

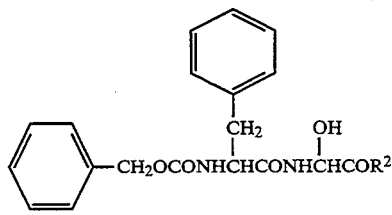

(IIIa)

wherein R² has the same meaning as above.

More particularly, the compound of the formula (IV) is dissolved or suspended in an organic solvent. The glyoxylic acid of the formula (VI) is added to the mixture while agitating at 0° to 30° C. and reacted for 50 to 240 hours. The product is concentrated under reduced pressure to obtain a white crystal of the formula (IIIa).

(e) The step comprising reacting the compound of the formula (IIIa) with acetic anhydride to thereby obtain the compound of the formula (IIIb).

More particularly, the compound of the formula (IIIa) is agitated for 1 to 48 hours at 0° to 30° C. in acetic anhydride and pyridine and then the reaction mixture is extracted with ethyl acetate. The resulting solution is washed with hydrochloric acid, water, sodium hydrogencarbonate aqueous solution, distilled water, saturated saline solution, or the like. The organic layer is then concentrated to obtain an oily substance. The oily substance is purified by silica gel chromatography, and recrystallized to obtain the compound of the formula (IIIb) as a white crystal.

Using an antitumor agent in the form of a mixture with phenylalanine enhances the antitumor activity as compared to using an antitumor agent along. Further, compared to using the antitumor agent alone, using the present conjugate containing said antitumor agent greatly reduces the acute toxicity.

The present conjugate can be used in the form of, for example, syrups, injections, ointments, tablets, or the like. The present conjugate may be contained in the formulation in an amount of 0.1 to 99.5% by weight, preferably in an amount of 1 to 90% by weight. The formulation of the present conjugate may be administered orally or parenterally. A dose varies with the method of administration, the extent of the treatment, and also the kind of antitumor substance contained therein. Generally speaking, however, the dose of the present conjugate is in the range of 100 to 1000 mg/kg/day orally, or of 5 to 500 mg/kg/day parenterally, which is divided into 1 to 4 dosages in a day.

The novel present conjugate of the phenylalanine-glycine compound and the antitumor substance exhibits a superior antitumor activity compared with an antitumor substance administered singly, or the antitumor substance administered in the form of a mixture with phenylalanine.

EXAMPLES

The present invention now will be further illustrated by, but is by no means limited to, the following examples. The physicochemical data described in the following Examples were obtained by the following methods:

(1) Elemental Analysis

A Yanagimoto MT3-type automatic elemental analyzer was used and the decomposition gas was detected with a thermal conductivity type detector (TCD).

(2) Optical Rotation

A Nihon Bunko automatic polarimeter DIP-360 was used to measure the optical rotation for a solution of the present conjugate to determine the $[\alpha]_D$.

(3) NMR

A Nihon Denshi JNM-GSX500 was used.

(4) Infrared Absorption Spectrum

A Nihon Bunko A-202 apparatus was used to measure the infrared absorption spectrum by the KBr tablet method and to determine $v_{max}$.

(5) Thin Layer Chromatography

The Rf value was determined by a hexane-ethyl acetate system, butanol-acetic acid-pyridine-distilled water system, or 5% methanol-dichloromethane system.

(6) Melting Point

The melting point was measured by a Yanagimoto micro melting point detector (DSC).

Example 1

(1) Preparation of carbobenzoxy-L-phenylalanineamide (IV)

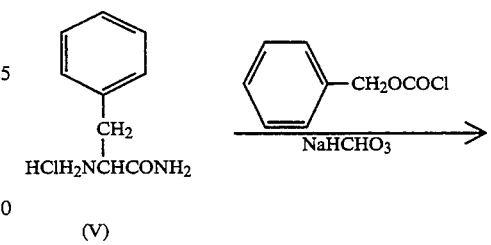

(V)

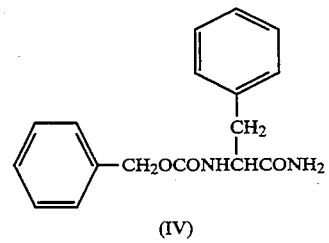

(IV)

L-phenylalanineamide hydrochloride (V) (1.00 g, 5.0 mmol) and 1.09 g of sodium hydrogencarbonate (13.0 mmol) were dissolved in 40 ml of distilled water. The solution was agitated at room temperature while adding 0.72 g of carbobenzoxychloride (4.2 mmol) and 25 ml of dichloromethane. After 2 hours, a further 0.72 g of carbobenzoxychloride (4.2 mmol) and 0.55 g of sodium hydrogencarbonate (6.5 mmol) were added. When agitation was continued, a white crystal was precipitated in the dichloromethane layer. To the crystal layer, dichloromethane was further added to completely dissolve them, and the dichloromethane was washed with a saturated sodium hydrogencarbonate solution. The dichloromethane layer was dried over anhydrous sodium sulfate, then concentrated under reduced pressure, and recrystallized with dichloromethane-hexane, whereby 1.46 g of a white compound (IV) was obtained. The physicochemical data of the product was as follows:

Yield: 99.0%,

Melting point: 160.1° to 162.1° C.

Elemental analysis (%) Found: C, 68.32; H, 5.93; N, 9.38 Calculated (for $C_{17}H_{18}N_2O_3$): C, 68.44; H, 6.08; N, 9.39

$[\alpha]_D$: −5.55° (c 1.0, $CH_3OH$)

$^1H$-NMR ($CDCl_3$): δ3.05 (dd, 1H, J=13.8 Hz, 7.3 Hz) phenylalanyl $CH_2$, δ3.13 (dd, 1H, J=13.8 Hz, 7.3

Hz) phenylalanyl CH$_2$, δ4.30 (m, 1H) NCHCO, δ5.09 (s, 2H) Ph-CH$_2$O, δ5.35 (br, 2H) CONH$_2$, δ5.66 (br, 1H) CONH$_2$ IR(KBr)$v_{max}$: 3425m, 3210s, 1690m, 1660s (amide group)

Rf: 0.42

5% methanol-dichloromethane (phosphomolybdic acid reagent UV+).

(2) Preparation of N-carbobenzoxy-L-phenylalanyl-D,L-2-hydroxyglycinebenzylester (IIIa-1)

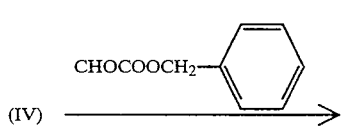

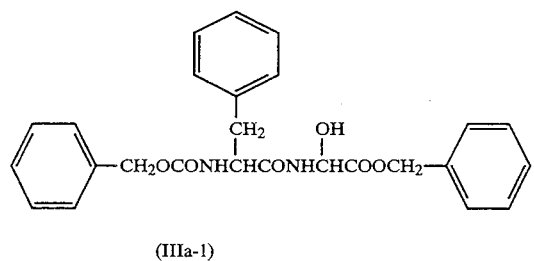

To a suspension of 2.81 g of carbobenzoxyphenylalanine amide (IV) (9.4 mmol) in dichloromethane, 1.93 g of benzyl glyoxylic acid (11.8 mmol) was added while agitating at room temperature and reacted for about 160 hours. The resulting suspension was concentrated under reduced pressure to obtain a crystal. The product was filtered with suction while washed with dichloromethane-hexane and then dried to give 3.78 g of the compound (IIIa-1).

Yield: 86.8%,

Melting point: 120.6° to 127° C.

Elemental analysis (%) Found: C, 67.00; H, 5.66; N, 6.77 Calculated (for C$_{26}$H$_{26}$N$_2$O$_6$): C, 67.52; H, 5.67; N, 6.06

[α]$_D$: −13.0° (c 1.0, CH$_3$OH)

$^1$H-NMR (CDCl$_3$): δ3.06 (m, 2H) phenylalanyl CH$_2$, δ3.86 (d, 0.5H) OH, δ3.97 (d, 0.5H) OH, δ4.43 (m, 1H) Ph-CH$_2$-CH, δ5.06 (m, 2H) Z group CH$_2$, 5.20 (m, 2H) benzylester CH$_2$, δ5.49 (t, 2H) glycyl CH, δ7.1 to 7.4 (m, 15H) aromatic ring IR(KBr)$v_{max}$: 3420m (NH), 3310s (NH), 1750m (COO), 1695m, 1660s (CONH)

Rf: 0.45

5% methanol-dichloromethane (phosphomolybdic acid reagent UV+).

(3) Preparation of N-carbobenzoxy-L-phenylalanyl-D,L-2-acetoxyglycinebenzylester (IIIb-1)

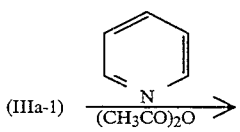

-continued

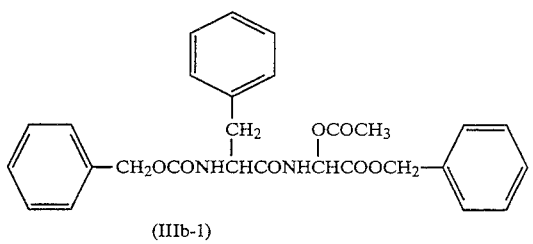

N-carbobenzoxy-L-phenylalanine-D,L-2-hydroxyglycinebenzylester (IIIa-1) (4.82 g, 10.4 mmol) was dissolved at room temperature in 50.0 ml of acetic anhydride and 36.5 ml of pyridine and agitated for about 24 hours. After the end of the reaction had been confirmed by thin layer chromatography, the reaction mixture was extracted with 100 ml of ethyl acetate and the organic layer was washed three times with 100 ml of distilled water, then twice with 100 ml of saturated saline solution. The washed organic layer was dried over anhydrous sodium sulfate and concentrated under reduced pressure to obtain 5.64 g of a yellow oily substance. The resulting oily substance was purified by silica gel chromatography using n-hexane/ethyl acetate (2/1) and recrystallized from ethyl acetate-n-hexane to obtain 1.31 g of the compound (IIIb-1).

Yield: 34.0%,

Melting point: 112.5° to 114.0° C.

Elemental analysis (%) Found: C, 66.63; H, 5.52; N, 5.68 Calculated (for C$_{28}$H$_{28}$N$_2$O$_7$): C, 66.66; H, 5.59; N, 5.55

[α]$_D$: −7.0° (c 1.0, CH$_3$OH)

$^1$H-NMR (CDCl$_3$): δ2.05 (s, 3H) acetyl CH$_3$, δ3.07 (m, 2H) phenylalanyl CH$_2$, δ4.46 (m, 1H) phenylalanyl N-CHCO, δ5.06 (m, 2H) Z group CH$_2$, δ5.19 (m, 2H) benzylester CH$_2$, δ6.37 (d, 1H) glycyl CH, δ7.1 to 7.4 (m, 15H) aromatic ring IR(KBr)$v_{max}$: 3300s (NH), 3060w, 3030w, 2973w, 1770s, 1740s, 1695s, 1665s Rf: 0.42

Hexane: Ethyl acetate=2:1 (phosphomolybdic acid reagent UV+).

(4) Preparation of N-carbobenzoxy-L-phenylalanyl-2-(5-fluorouracil-1-yl-D,L-glycinebenzylester (II-1)

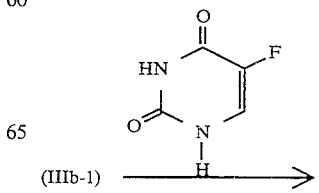

-continued

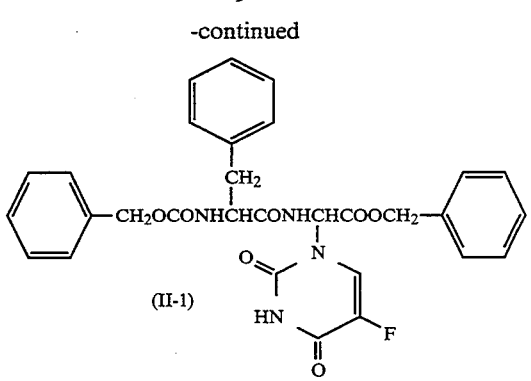

N-carbobenzoxy-L-phenylalanyl-D,L-2-acetoxy-glycinebenzylester (IIIb-1) (0.25 g, 0.5 mmol) and 73.5 mg of 5-fluorouracil (0.57 mmol) were dissolved in 1.0 ml of dimethylformamide at room temperature and 0.51 g of triethylamine (5.0 mmol) was added and the mixture was agitated for about 20 minutes. After the end of the reaction had been confirmed by thin layer chromatography, the reaction mixture was concentrated under reduced pressure and extracted with 50 ml of ethyl acetate. The organic layer was washed with 20 ml of distilled water and 40 ml of saturated saline solution. The washed layer was dried over anhydrous sodium sulfate, concentrated under reduced pressure, and recrystallized from ethyl acetate-n-hexane to obtain 0.16 g of the compound (II-1).

Yield: 53.1%,
Melting point: 170.3° to 175.0° C.
Elemental analysis (%) Found: C, 62.68; H, 4.68; N, 9.76 Calculated (for $C_{30}H_{27}N_4O_7F$): C, 62.71; H, 4.74; N, 9.75
$[\alpha]_D$: −7.0° (c 1.0, $CH_3OH$)
$^1$H-NMR ($CDCl_3$): δ2.8 to 3.0 (m, 1.5H) diastereomeric phenylalanyl $CH_2$, δ3.12 (dd, 0.5H, J=13.8, 5.9 Hz), δ4.67 (d, 0.5H, J=7.3 Hz) phenylalanyl CHCO, δ4.73 (d, 0.5H, J=6.4 Hz) phenylalanyl CHCO, δ4.9 to 5.2 (m, 4H) benzyl $CH_2$, δ5.51 (d, 0.5H), δ5.57 (d, 0.5H), δ5.80 (d, 0.5H) glycyl CH, δ5.84 (d, 0.5H) glycyl CH, δ7.0 to 7.3 (m, 15H) aromatic ring, δ7.50 (d, 0.5H, J=5.5 Hz) uracil 6H, δ7.60 (d, 0.5H, J=5.5 Hz) uracil 6H, δ9.19 (br, 0.5H) uracil 3NH, δ9.66 (br, 0.5H) uracil 3NH IR (KBr)$\nu_{max}$: 3405m, 3300s, 3160m, 3140m, 1760s, 1700s, 1660s.

(5) Preparation of L-phenylalanyl-2-(5-fluorouracil-1-yl)-D,L-glycine (I-1).

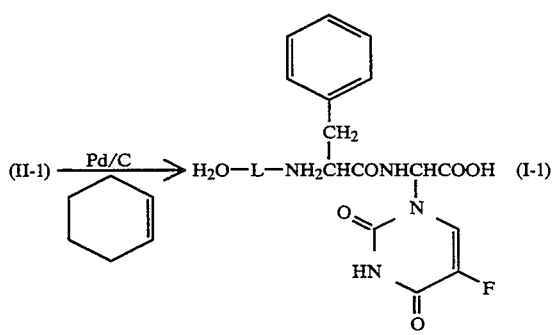

Methanol was added dropwise to 246.5 mg of 10% palladium carbon at 0° C. To the resulting suspension was added dropwise at 0° C. a solution of 0.29 g of N-carbobenzoxy-L-phenylalanyl-2-(5-fluorouracil-1-yl)-D,L-glycinebenzylester (II-1) (0.5 mol) in a mixture of methanol and cyclohexene. The solution was heated under reflux at 70° to 80° C. for about 20 minutes. After the end of the reaction had been confirmed by thin layer chromatography, the reaction liquid was diluted with methanol and filtered through a fluted filter paper. The filtrate was concentrated under reduced pressure to obtain a white crystal. The crystal was washed with ethyl acetate to obtain 0.16 g of the compound (I-1).

Yield: 89.6%,
Melting point: 197.3° to 201.3° C.
Elemental analysis Found: C, 48.8; H, 4.5; N, 14.8 Calculated (for $C_{15}H_{15}O_5N_4F\cdot H_2O$): C, 48.9; H, 4.7; N, 15.2
$[\alpha]_D$: 11.9° (c 2.0, $CH_3OH$)
$^1$H-NMR ($D_2O$): δ2.93 to 2.97 (dd, 2H) diastereomeric phenylalanine $CH_2$, δ3.20 to 3.29 (dd, 2H) diastereomeric phenylalanine $CH_2$, δ4.26 to 4.33 (m, 2H), δ5.79 (s, 1H) glycyl CH, δ5.90 (s, 1H) glycyl CH, δ7.0 to 7.3 (m, 10H) aromatic ring, δ7.55 (d, 1H, J=6 Hz) uracil 6H, δ7.85 (d, 1H, J=6 Hz) uracil 6H IR (KBr)$\nu_{max}$: 3400m, 3170m, 3030m, 2800m, 1690s, 1500m, 1370s, 1240s Rf: 0.62, 0.57
Butanol: Acetic acid: Pyridine: Distilled water=4:1:1:2 (ninhydrin reagent UV+).

(6) The procedures of Examples 1 (4) and (5) were repeated, except that 5-[bis(2-chloroethyl)amino]uracil was used instead of 5-fluorouracil, to obtain L-phenylalanyl-2-[5-(bis(2-chloroethyl)amino)uracil-1-yl]-D,L-glycine at a yield of 45%. The results of the elemental analysis were as follows:

Found: C, 48.01; H, 4.73; N, 15.02
Calculated (for $C_{19}H_{23}O_5N_5Cl_2$): C, 48.32; H, 4.91; N, 14.83.

Example 2

(1) Preparation of N-carbobenzoxy-L-phenylalanyl-D,L-2-hydroxyglycineethylester (IIIa-2)

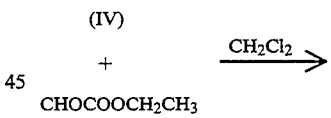

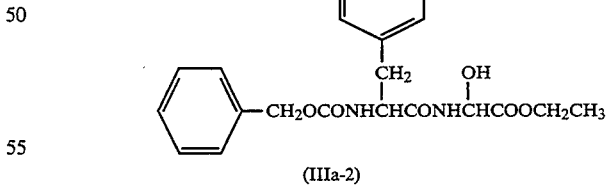

To a suspension of 0.94 g of carbobenzoxy-phenylalanineamide (IV) (3.1 mmol) prepared from Example 1(1) in dichloromethane, 0.40 g of ethyl glyoxylate (3.9 mmol) was added while agitating at room temperature, and then the suspension was agitated for about 160 hours. The suspension was concentrated under reduced pressure to obtain a white crystal. The crystal was filtered with suction while washing with dichloromethane-hexane and then dried to obtain 3.78 g of the compound (IIIa-2).

Yield: 77.6%,

Melting point: 143.7° to 148.7° C.

Elemental analysis (%) Found: C, 61.60; H, 5.72; N, 7.02 Calculated (for $C_{21}H_{24}N_2O_6$): C, 62.99; H, 6.04; N, 7.00

$[\alpha]_D$: 6.85° (c 1, DMSO)

$^1$H-NMR (d$_6$-DMSO): $\delta$1.19 (t, 3H, J=6.91) ethylester CH$_3$, $\delta$2.74 (m, 1H) phenylalanyl CH$_2$, $\delta$2.98 (m, 1H) phenylalanyl CH$_2$, $\delta$4.13 (m, 2H) ethylester CH$_2$, $\delta$4.31 (m, 1H) phenylalanyl CH, $\delta$4.93 (d, 2H, J=3.33) Z group CH$_2$, $\delta$5.49 (t, 2H) glycyl CH, $\delta$6.60 (d, 0.5H, J=6.67) OH, $\delta$6.68 (d, 0.5H, J=6.67) OH, $\delta$7.19 to 7.34 (m, 10H) aromatic ring IR(KBr)$v_{max}$: 3300s, 3060m, 3030m, 2950w, 1747s, 1685s, 1658s, 1530s Rf: 0.32

5% methanol-dichloromethane (phosphomolybdic acid reagent UV+).

(2) Preparation of N-carbobenzoxy-L-phenylalanyl-D,L-2-acetoxyglycineethlester (IIIb-2)

(IIIa-2) $\xrightarrow{(CH_3CO)_2O}$ N (IIIb-2)

N-carbobenzoxy-L-phenylalanine-D,L-2-hydroxy-glycineethylester (IIIa-2) (2.65 g, 6.6 mmol) was dissolved in 31.8 ml of acetic anhydride and 23.2 ml of pyridine at room temperature and agitated for about 3 hours. After the end of the reaction had been confirmed by thin layer chromatography, the reaction mixture was extracted with 70 ml of ethyl acetate and the organic layer was washed three times with 70 ml of distilled water and then twice with 70 ml of saturated saline solution. The washed organic layer was dried over anhydrous sodium sulfate, then concentrated under reduced pressure to obtain 2.31 g of a yellow oily substance. The oily substance was purified by silica gel chromatography (n-hexane/ethyl acetate=2/1), and recrystallized (ethyl acetate-hexane) to obtain 1.18 g of the compound (IIIb-2).

Yield: 40.3%,

Melting point: 141.5° to 147.0° C.

Elemental analysis (%) Found: C, 62.13; H, 5.65; N, 6.32 Calculated (for $C_{23}H_{26}N_2O_7$): C, 62.43; H, 5.92; N, 6.33

$[\alpha]_D$: 23.55° (c 1, CHCl$_3$)

$^1$H-NMR (CDCl$_3$): $\delta$1.27 (t, 3H, J=7.10) ethylester CH$_3$, $\delta$2.08 (s, 1H) acetyl CH, $\delta$3.11 (m, 2H) phenylalanyl CH$_2$, $\delta$4.22 (m, 2H) ethylester CH$_2$, $\delta$4.49 (br, 1H) phenylalanyl CHCO, $\delta$5.09 (s, 2H) Z group CH$_2$, $\delta$5.23 (br, 1H) phenylalanyl CONH, $\delta$6.32 (d, 1H, J=9.16) glycyl CH, $\delta$7.16 to 7.37 (m, 10H) aromatic ring IR (KBr)$v_{max}$: 3300s, 3050w, 3030w, 2960m, 1735s, 1690m, 1660s, 1540m Rf: 0.54

Hexane: Ethyl acetate=1:1 (phosphomolybdic acid reagent UV+).

(3) Preparation of N-carbobenzoxy-L-phenylalanyl-2-(5-fluorouracil-1-yl)-D,L-glycineethylester (II-2)

(IIIb-2) $\longrightarrow$ (II-2)

N-carbobenzoxy-L-phenylalanyl-D,L-2-acetoxy-glycineethylester (IIIb-2) (0.47 g, 1.1 mmol) and 0.15 g of 5-fluorouracil (1.20 mmol) were dissolved in 2.2 ml of dimethylformamide at room temperature and then 1.06 g of triethylamine (10.5 mmol) was added thereto. The mixture was agitated at room temperature for about 20 minutes. After the end of the reaction had been confirmed by thin layer chromatography, the reaction mixture was concentrated under reduced pressure and the residue was extracted with 100 ml of ethyl acetate. The extracted organic layer was washed with 40 ml of distilled water and 80 ml of saturated saline solution. The washed organic layer was dried over anhydrous sodium sulfate, concentrated under reduced pressure, and recrystallized (ethyl acetate-hexane) to obtain 0.54 g of the compound (II-2).

Yield: 90.7%,

Melting point: 98.0° to 102.3° C.

Elemental analysis (%) Found: C, 57.98; H, 4.94; N, 10.56 Calculated (for $C_{25}H_{25}N_4O_7F$): C, 58.59; H, 4.92; N, 10.93

$[\alpha]_D$: −10.32° (c 2, CHOH)

$^1$H-NMR (CDCl$_3$): $\delta$1.19 (t, 1.5H, J=7.11) ethylester CH$_3$, $\delta$1.25 (t, 1.5H, J=7.11) ethylester CH$_3$, $\delta$3.01 (m, 1.5H) phenylalanyl CH$_2$, $\delta$3.15 (dd, 0.5H, J=13.75, 5.96 Hz) phenylalanyl CH$_2$, $\delta$4.24 (m, 2H) ethylester CH$_2$, $\delta$4.67 (d, 0.5H, J=7.3 Hz) phenylalanyl CHCO, $\delta$4.73 (d, 0.5H, J=6.4 Hz) phenylalanyl CHCO, $\delta$5.05 (m, 2H) Z group CH$_2$, $\delta$5.63 (d, 0.5H, J=8.25 Hz) phenylalanyl CONH, $\delta$5.70 (d, 0.5H, J=8.25 Hz) phenylalanyl CONE, $\delta$5.78 (d, 0.5H, J=7.33 Hz) glycyl CH, $\delta$5.83 (d, 0.5H, J=7.33 Hz) glycyl CH, $\delta$7.05 to 7.31 (m, 10H) aromatic ring, $\delta$7.56 (d, 0.5H, J=5.04 Hz) uracil CH, $\delta$7.65 (d, 0.5H, J=5.04 Hz) uracil CH, $\delta$9.70 (br, 0.5H) uracil NH, $\delta$10.0 (br, 0.5H) uracil NH IR (KBr)$v_{max}$: 3300s, 3050m, 3020m, 1750s, 1700s, 1660s, 1510m Rf: 0.26

Hexane: Ethyl acetate=1:1 (phosphomolybdic acid reagent UV+).

(4) Preparation of L-phenylalanyl-2-(5-fluorouracil-1-yl)-D,L-glycineethylester (I-2)

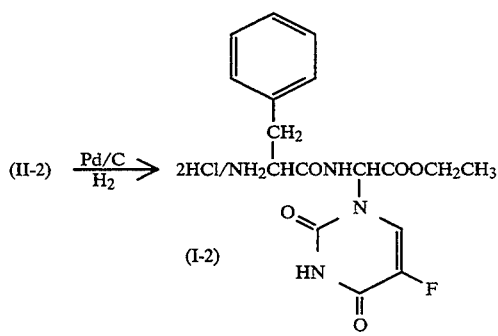

A 0.1N hydrochloric acid-methanol solution was added dropwise to 98.6 mg of 10% palladium carbon at 0° C. Further, a 0.1N hydrochloric acid-methanol solution (total volume of 4.7 ml) of 0.10 g (0.2 mmol) of N-carbobenzoxy-L-phenylalanyl-2-(5-fluorouracil-1-yl)-D,L-glycineethylester (II-2) was added thereto dropwise and then the mixture was agitated under an H₂ gas stream at room temperature for 3 hours. After the end of the reaction had been confirmed by thin layer chromatography, the reaction mixture was diluted with methanol and filtered through a fluted filter paper. The filtrate was concentrated under reduced pressure to obtain a white crystal. The crystal was washed with diethylether and filtered to obtain 65.4 g of the compound (I-2).

Yield: 72.4%,

Melting point: 174.0° to 185.3° C.

Elemental analysis (%) Found: C, 45.72; H, 4.66; N, 12.41 Calculated (for $C_{17}H_{19}O_5N_4F \cdot 2HCl$): C, 45.25; H, 4.69; N, 12.41

$[\alpha]_D$: 27.03° (c 1, $CH_3OH$)

¹H-NMR ($D_2O$): δ1.31 (t, 1.5H, J=7.10 Hz) ethylester $CH_3$, δ1.36 (t, 1.5H, J=7.10 Hz) ethylester $CH_3$, δ3.12 (dd, 0.5H, J=13.29, 10.54 Hz) phenylalanyl $CH_2$, δ3.38 (m, 1H) phenylalanyl $CH_2$, 3.47 (dd, 0.5H, J=13.29, 5.50 Hz) phenylalanyl $CH_2$, δ4.37 (m, 2H) ethylester $CH_2$, 4.47 (m, 1H) phenylalanyl CHCO, δ6.36 (d, 1H, J=7.33 Hz) glycyl CH, δ7.26 to 7.54 (m, 5H) aromatic ring, δ7.90 (d, 0.5H, J=5.5 Hz) uracil CH, δ8.05 (d, 0.5H, J=5.5 Hz) uracil CH IR(KBr)$\nu_{max}$: 3420m, 3180m, 3020s, 1705s, 1530m, 1495m, 1470m Rf: 0.24

5% methanol-dichloromethane (phosphomolybdic acid reagent UV+).

Example 3

(1) Preparation of N-carbobenzoxy-L-phenylalanyl-2-[p-(bis(2-chloroethyl)amino)-L-phenylalaninemethylester-2-yl]-D,L-glycineethylester (II-3)

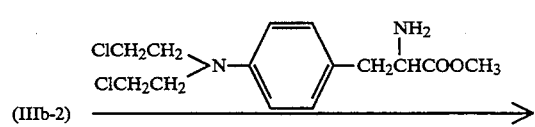

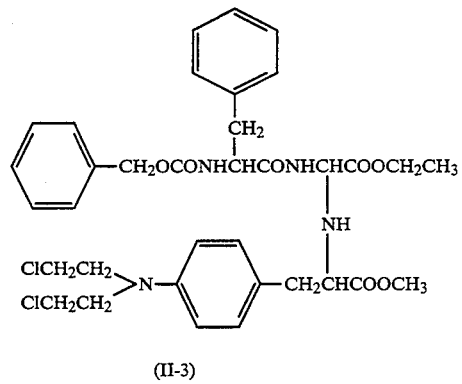

The compound (IIIb-2) obtained from Example 2(2) was reacted with melphalan methylester [p-(bis(2-chloroethylamino)-L-phenylalaninemethylester] in the manner same as that in Example 2(3) to obtain the compound (II-3). The melphalan methylester was treated with a sodium hydrogen carbonate solution (2.2 equivalents) to remove the hydrochloride and extracted with dichloromethane.

Yield: 84.3%,

Melting point: 112.3° to 115.3° C.

Elemental analysis (%) Found: C, 60.04; H, 6.00; N, 7.93 Calculated (for $C_{35}H_{42}O_7N_4Cl_2$): C, 59.91; H, 6.03; N, 7.98

$[\alpha]_D$: 19.1° (c 1, $CHCl_3$)

¹H-NMR ($CDCl_3$): δ1.26 (t, 3H, J=7.10 Hz) ethylester $CH_3$, δ2.73 (dd, 0.5H, J=13.75, 7.79 Hz) phenylalanine $CH_2$, δ2.91 (dd, 0.5H, J=13.98, 5.73 Hz) phenylalanine $CH_2$, δ3.05 (m, 2H) melphalan Ph-$CH_2$, δ3.57 to 3.62 (m, 4H) melphalan $CH_2$-$CH_2$, δ3.65 to 3.70 (m, 4H) melphalan Cl-$CH_2$, δ3.69 (s, 3H) melphalan $CH_3$, δ4.14 (m, 2H) ethylester $CH_2$, δ4.36 (m, 1H) melphalan CH-CO, δ5.07 (m, 2H) Z group $CH_2$, δ5.18 (m, 1H) melphalan NH, δ6.59 (d, 1H, J=8.71 Hz) glycyl CH, δ6.96 to 7.31 (m, 14H) aromatic ring IR(KBr)$\nu_{max}$: 3300s, 3070m, 3040m, 2950m, 1730s, 1645s, 1610m, 1520s Rf: 0.50, 0.56

Hexane: Ethyl acetate=1:1 (phosphomolybdic acid reagent UV+).

(2) Preparation of L-phenylalanyl-2-[p-(bis(2-chloroethyl)amino)-L-phenylalaninemethylester-2-yl]-D,L-glycineethylester (I-3)

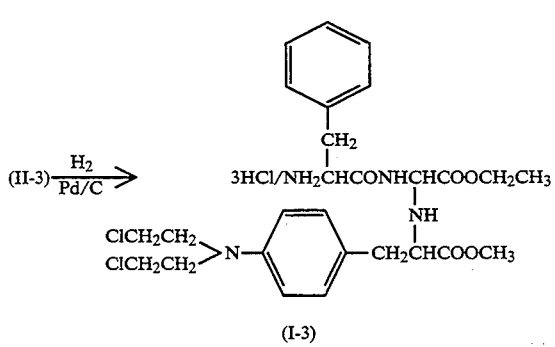

The compound (II-3) obtained from Example 3 (1) was reacted with palladium carbon under an H₂ stream in the manner same as that in Example 2(4), to obtain the compound (I-3).

Yield: 89.7%,
Melting point: 102.3° to 108.0° C.
Elemental analysis (%) Found: C, 47.33; H, 5.97; N, 8.16 Calculated (for $C_{27}H_{36}O_5N_4Cl\cdot 3HCl$): C, 47.90; H, 5.80; N, 8.28

$[\alpha]_D$: 36.5° (c 1, $CH_3OH$)

$^1$H-NMR ($D_2O$): $\delta 1.25$ (t, 3H, J=7.10 Hz) ethylester $CH_3$, 3.17 (m, 2H) phenylalanyl $CH_2$, $\delta 3.27$ (m, 2H) melphalan Ph-$CH_2$, $\delta 3.70$ to 3.76 (m, 4H) melphalan $CH_2$—$CH_2$—, $\delta 3.86$ to 3.90 (m, 4H) melphalan Cl—$CH_2$, $\delta 3.89$ (s, 3H) melphalan $CH_3$, $\delta 4.37$ (m, 2H) ethyl ester $CH_2$, 4.55 (m, 1H) melphalan CH—CO, $\delta 7.35$ to 7.71 (m, 9H) aromatic ring IR(KBr)$\upsilon_{max}$: 3410s, 3150m, 2950s, 1740s, 1705s, 1610m Rf: 0.38, 0.44

5% methanol-dichloromethane (phosphomolybdic acid reagent UV+).

Example 4: Acute Toxicity (1) The conditions in the feeding chamber were arranged to a temperature of 23°±1° C., a relative humidity of 55±5%, a ventilation frequency of 20 times per hour, and a lighting term of 12 hours. Wistar rats (male; five-week old;. 120 to 141 g) were used. The rats were placed in metallic cages having wire walls in the front and bottom thereof, at the rate of 5 rats per one cage. They were allowed food (MF: Oriental Yeast) and water ad libitum.

(2) Method of Administration

The conjugate (I-1) of the present invention obtained from Example 1(5) was suspended in a 1.5% methylcellulose aqueous solution. The suspension was administered by force. The amount of the administration was 1 ml per 100 g body weight of animals forced to fast for 18 hours, that is, 250 mg/kg was administered. Symptoms of addiction and survival were observed hourly up to 8 hours after the administration, then twice a day until 14 days after administration. No death was observed.

Example 5: Antitumor Activity

The concentration of the solid tumor cells (Sarcoma-180) was aseptically adjusted to $1\times 10^6/0.2$ ml with a medium [prepared by filtering 10% bovine fetal serum-added MEM (Eagles' Minimum Essential Medium) for sterilization, and stored at 4° C.] and subcutaneously implanted at the axillas of ICR mice (5 weeks old; females; one group consisting of 10 mice). From the next day, the samples (0.15% physiological saline solution) shown in Table 1 were administered intraperitoneally 10 times every other day. On the 22nd day, the tumors were excised and the inhibition rate (IR) was obtained from the weight of the tumors. The results are shown in Table 1. The inhibition rate (IR) (%) was calculated by the following formula:

$$IR\ (\%) = 1-(T/C)\times 100$$

wherein T is the average tumor weight of the treated group, and C is the average tumor weight of the control group.

TABLE 1

| Group | Amount (mg/kg) | Average tumor weight ± SD | IR (%) |
|---|---|---|---|
| Control | — | 3.438 ± 1.481 | — |
| 5-Fu | 15 | 1.467 ± 1.437 | 57.3 |
| MP | 10 | 1.358 ± 1.369 | 60.5 |
| 5-CAU | 10 | 1.574 ± 1.285 | 54.2 |
| Phe + 5-Fu | 15 + 15 | 1.385 ± 1.297 | 59.7 |
| Phe + MP | 15 + 10 | 1.407 ± 1.295 | 59.1 |
| Phe + 5-CAU | 15 + 10 | 1.550 ± 1.375 | 54.9 |
| Phe-5-Fu | 30 | 0.770 ± 0.397 | 77.6 |
| Phe'-5-Fu | 30 | 0.808 ± 0.389 | 76.5 |
| Phe-MP | 20 | 0.943 ± 0.587 | 72.6 |
| Phe-5-CAU | 20 | 0.854 ± 0.664 | 75.2 |

5-Fu: 5-Fu alone
MP: Melphalan alone
5-CAU: 5-[bis(2-chloroethyl)amino]uracil alone
Phe + 5-Fu: Mixture of L-phenylalanine and 5-Fu
Phe + MP: Mixture of L-phenylalanine and MP
Phe + 5-CAU: Mixture of L-phenylalanine and 5-CAU
Phe-5-Fu: Present Conjugate (I-1) prepared from Example 1
Phe'-5-Fu: Present Conjugate (I-2) prepared from Example 2
Phe-MP: Present Conjugate (I-3) prepared from Example 3
Phe-5-CAU: Present Conjugate prepared from Example 1(6).

Example 6: Preparation of Injection

A 500 mg amount of the compound (I-1) of the present invention obtained from Example 1(5) was dissolved in 50 ml of ethanol to prepare an injection.

Although the present invention has been described with reference to specific embodiments, various changes and modifications obvious to those skilled in the art are deemed to be within the spirit, scope, and concept of the invention.

We claim:

1. A phenylalanine-glycine compound of formula (I):

wherein R represents an antitumor substance, or a salt or an ester thereof.

2. A compound, or a salt or an ester thereof according to claim 1, wherein the antitumor substance is an antimetabolic antitumor substance.

3. A compound, or a salt or an ester thereof according to claim 2, wherein the antimetabolic antitumor substance is 5-fluorouracil.

4. A compound, or a salt or an ester thereof according to claim 1, wherein the antitumor substance is an alkylating antitumor substance.

5. A compound, or a salt or an ester thereof according to claim 4, wherein the alkylating antitumor substance is 5-[bis(2-chloroethyl)amino]-uracil.

6. A compound, or a salt or an ester thereof according to claim 4, wherein the alkylating antitumor substance is p-[bis (2-chloroethyl)amino]-L-phenylalanine.

7. A pharmaceutical composition comprising a phenylalanine-glycine compound of the formula (I):

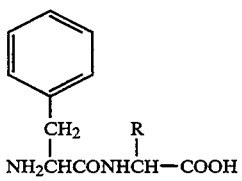

wherein R represents a residue of an antitumor substance, or a pharmaceutically acceptable salt or ester thereof, and a pharmaceutically acceptable carrier.

8. A composition according to claim 7, which is an antitumor agent.

9. A composition according to claim 7, wherein the antitumor substance is an antimetabolic antitumor substance.

10. A composition according to claim 9, wherein the antimetabolic antitumor substance is 5-fluorouracil.

11. A composition according to claim 7, wherein the antitumor substance is an alkylating antitumor substance.

12. A composition according to claim 11, wherein the alkylating antitumor substance is 5-[bis(2-chloroethyl)amino]-uracil.

13. A composition according to claim 11, wherein the alkylating antitumor substance is p-[bis(2-chloroethyl)amino]-L-phenylalanine.

14. A method of treating tumor in an animal, comprising administering to the animal a composition comprising a phenylalanine-glycine of the formula (I):

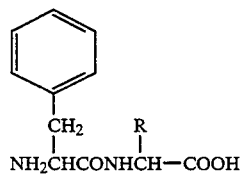

wherein R represents an antitumor substance, or a pharmaceutically acceptable salt or ester thereof.

* * * * *

UNITED STATES PATENT AND TRADEMARK OFFICE
CERTIFICATE OF CORRECTION

PATENT NO. : 5,411,964
DATED : May 2, 1995
INVENTOR(S) : Koichi Niimura et al

It is certified that error appears in the above-indentified patent and that said Letters Patent is hereby corrected as shown below:

Column 1, line 32, delete "general" and insert therefor --normal--;
line 40, delete "penrose" and insert therefor --pentose--;
line 59, delete "penrose" and insert therefor --pentose--.

Column 4, line 45, delete "L-phenylalanineamide" and insert therefor --L-phenylalanine amide--.

Column 6, line 19, delete "L-phenylalanineamide" and insert therefor --L-phenylalanine amide--;
line 43, delete "L-phenylalanineamide" and insert therefor --L-phenylalanine amide--.

Column 10, line 59, delete "phenylalanineamide" and insert therefor --phenylalanine amide--.

Column 17, claim 7, line 11, delete "a residue of".

Column 18, claim 14, line 12, before "of" insert --compound--.

Signed and Sealed this

Twenty-fourth Day of October, 1995

BRUCE LEHMAN

*Attest:*

*Attesting Officer*  *Commissioner of Patents and Trademarks*